United States Patent [19]

Vofsi et al.

[11] 4,325,727
[45] * Apr. 20, 1982

[54] PLANT GROWTH REGULANT PHOSPHONOACETALS

[75] Inventors: David Vofsi; Martin M. Halmann; Shaul Yanai, all of Rehovot, Israel

[73] Assignee: Yeda Research and Development Company, Ltd., Rehovot, Israel

[ * ] Notice: The portion of the term of this patent subsequent to Jun. 10, 1997, has been disclaimed.

[21] Appl. No.: 37,111

[22] Filed: May 8, 1979

Related U.S. Application Data

[63] Continuation-in-part of Ser. No. 858,901, Aug. 12, 1977, Pat. No. 4,207,417.

[51] Int. Cl.³ .................... A01N 57/16; C07H 13/00; C07D 319/04; C07D 317/12
[52] U.S. Cl. .......................................... 71/86; 536/53; 536/117; 260/338; 260/340.7; 260/340.9 R
[58] Field of Search .................. 536/117, 53; 71/86; 260/338, 340.7, 340.9 R

[56] References Cited

U.S. PATENT DOCUMENTS

| | | | |
|---|---|---|---|
| 3,524,846 | 8/1970 | Moffatt et al. | 536/117 |
| 3,837,834 | 9/1974 | Hill et al. | 71/86 |
| 3,879,188 | 4/1975 | Fritz et al. | 71/86 |
| 4,207,417 | 6/1980 | Vofsi et al. | 536/117 |

OTHER PUBLICATIONS

Yanai et al. Journal of the Chemical Society, (1978), pp. 511-516-Perrin II.

*Primary Examiner*—Catherine L. Mills
*Attorney, Agent, or Firm*—Browdy and Neimark

[57] ABSTRACT

Phosphonoacetals of the formula

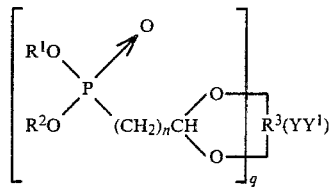

wherein
$R^1$ is an alkyl group having from 1-3 carbon atoms;
$R^2$ is a hydrogen atom or a cation such as $NH_4^+$, $Na^+$, $K^+$, $Ca^{2+}$, $Sn^{2+}$, $Zn^{2+}$, $Cd^{2+}$, $Cu^{2+}$, and $R^1$;
n is an integer from 0 to 2;
q is an integer from 1 to 3;
$R^3$ is a residue of a polyhydroxy compound having from 2-12 carbon atoms;
Y and $Y^1$ are each selected from the group consisting of hydrogen atoms, hydroxyl groups, carbinol groups, methyl halogens, methyl carbamoyls.

15 Claims, No Drawings

PLANT GROWTH REGULANT PHOSPHONOACETALS

FIELD OF THE INVENTION

This application is a Continuation-In-Part of patent application Ser. No. 858,901, filed Aug. 12, 1977, now U.S. Pat. No. 4,207,417

The present invention is directed to novel phosphorus substituted cyclic acetals, including hydroxyl and halogen substituted derivatives, to a method of preparation of same, and to their use as plant growth regulators. Some of these compounds have been previously described by us (U.S. Pat. Appl. Ser. No. 858,901) as potential flame-retardent non-reactive and reactive ingredients in polyurethane compositions, polyesters and acrylics, including the flame retardation of synthetic fibers. Some others of these new compounds have a valuable use as lubricating oil additives.

STATE OF THE PRIOR ART

Plant growth regulators are natural or synthetic organic compounds which, when applied to the plant, are able to change their physiological processes, and thus enabling enhancement of yields, quality, easier harvesting, etc.

Several organophosphorus compounds have been found to exercise plant-growth regulatory effects. Two of the better known compounds of this class are glyphosine

and 2-chloroethylphosphonic acid $(ClCH_2CH_2P(O)(OH)_2)$.

SUMMARY OF THE INVENTION

We found several derivatives of the basic cyclic phosphonoacetal family to be non-toxic to the plant tissues and at the same time to show outstanding activity as stimulators of cell division in plants.

The evaluation of their activity is based on screening cell cultures which are homogeneous, axenic, cuticle free systems with almost all cells metabolically active, and which are known to mirror the behaviour in heterogeneously differential plants. To enhance the versatility of our results the tests were carried out on chlorophyllous as well as achlorophylous cultures.

It is the object of the present invention to extend the previous application to cyclic phosphonoacetals which do not have functional group substitutions on the acetal ring, as well as others which have such substitutions, including halogens, hydroxyls and other common derivatives based on these.

Another object is to describe phosphonoacetal derivatives being salts or free acids obtained by the base-catalysed hydrolysis of the above mentioned phosphonoesters.

A particularly important use of these compounds is in preparing flame retardant polyurethanes, cellulosic polymers, polyesters and cotton-polyesters blends. In addition to the chain-extended phosphonoacetalated polyols described in the previous application, these compounds may be also used as additives in different polymeric compositions.

A further object is to describe some of the cyclic phosphonoacetals and especially those having the 1,3-dioxan configuration, as potential plant growth regulators.

A still further use of several cyclic phosphonoacetals is as water dispersible wetting and suspending agents as well as valuable lubricating oil additives.

DESCRIPTION OF THE PREFERRED EMBODIMENT

The compounds of the invention are phosphonoacetals of the formula:

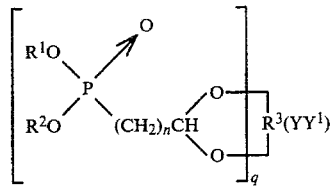

wherein
$R^1$ is an alkyl group having from 1-3 carbon atoms;
$R^2$ is a hydrogen atom or a cation such as $NH_4^+$, $K^+$, $Ca^{2+}$, $Sn^{2+}$, $Zn^{2+}$, $Cd^{2+}$, $Cu^{2+}$, and $R^1$;

The specific examples given come to indicate the versatility of their uses and have to be judged as illustrative only, since many modifications on the functional groups on the phosphonoacetal backbone are possible; such modifications within the spirit of the present invention will be evident to people involved in this art from the detailed descriptions.

EXAMPLE 1

Galactitol (4 parts) is reacted with 0,0-diethyl-2,2-diethoxyethylphosphonate (6.45 parts) in the presence of concentrated hydrochloric acid (10 parts) at room temperature for 5 days. After neutralization, the reaction mixture is extracted by chloroform (3×50 parts). The organic layer yields after solvent extraction a syrupy mixture of diphosphonoacetals of galactitol (11.1 parts, 99%). Treating by ether and leaving overnight at 5° precipitates 2.25 parts of shiny crystals, m.p. 174°–6°. Found: C, 42.4; H, 7.0; P, 12.2; Calc. for $C_{18}H_{36}O_{12}P_2$: C, 42.7, H, 7.1, P, 12.25%, identified by I.R., N.M.R., and M.S. as 1,3:4,6-di-O-diethyl-phosphonomethylgalactitol. The syrup which is left after its separation is passed through a silicic acid column (300 parts) and eluted, first by chloroform and then by chloroform (9): methanol (1), yielding a straw-coloured syrup (8.85 parts), $\eta_D^{25} 1.4605$, Found: P, 12.3; Calc.: P, 12.2% similarly proven to be the 1,3:4,5-di-O-diethylphosphonomethylgalactitol.

These 2 isomers are both nontoxic to white and green cultures, however the 1,3-:4,5 derivative shows a growth stimulation effect of about 17% on the green calli.

EXAMPLE 2

A run was carried out as in Example 1, but by reacting galactitol (1.8 parts) with 3,3-diethyl diethoxypropylphosphonate (5.5 parts). After treatment with ether of the chloroform extraction portion there were obtained 3.8 parts of a crystalline diphosphonoacetal, m.p. 91°–2°, Found: P, 11.4; Calc.: P, 11.6%, subsequently identified as the 1,3:4,6-di-O-diethylphosphonoethylgalactitol.

EXAMPLE 3

A reaction was carried out similar to that of Example 1 but with dimethyl 2,2-diethoxyethylphosphonate as the transacetalating agent. The crystalline product has a m.p. of 191°–2°. Found: C, 37.51; H, 6.55; P, 13.77. Calc. for $C_{14}H_{28}O_{12}P_2$: C, 37.33; H, 6.2; P, 13.78. Proved by N.M.R., I.R., and M.S. to be the 1,3:4,6-disubstituted phosphonoacetal.

EXAMPLE 4

A reaction was carried out as in Example 1 but with mannitol as the substrate. The product was obtained as colourless syrup, $\eta_D^{25}$ 1,468; Calc.: P, 12,2, Found: 12.9%. Proved by spectroscopic methods to be 1,3:4,6-di-O-diethylphosphonomethylmannitol.

EXAMPLE 5

A transacetalation reaction was carried out between ethylene glycol (6.2 parts) and 0,0-diethyl-2,2-diethoxyethylphosphonate (25.4 parts), in the presence of concentrated hydrochloric acid (10 parts), at room temperature, with magnetic stirring, for 24 hours. The product was isolated by vacuum distillation and obtained as an oil (7.9 parts, 35%), b.p. 79°–80° at Torr; 0.05 Torr; $\eta_D^{25}$ 1.445; %P 13.7, and was identified by its I.R., N.M.R. and M.S. to be 2-diethylphosphonomethyl-1,3-dioxolan. In a herbicidal activity test using cuticle-free sterile microcultures of both heterotrophic and phosynthetic plants (green and white calli), this product proved to be non-toxic, and had 20% effect of growth enhancement on white cultures and 11% on the green ones.

EXAMPLE 6

A run was carried out as in Example 5 but with propane-1,3-diol (7.6 parts) as the substrate and reacting for 4 hours; there was obtained an oil (18.3 parts, 78%), b.p. 96°–8° at 0.07 Torr; $n_D^{25}$ 1.448; %P, 13.15, which was similarly identified as the 2-diethylphosphonomethyl-1,3-dioxan derivative. This product, by the herbicidal activity test, proved to be non-toxic, and caused a growth enhancement of 47% on green cultures and 21% on the white ones.

EXAMPLE 7

A mixture of di-bromoneopentylglycol (13.1 parts) and 0,0-diethyl-2,2-diethoxyethylphosphonate (13 parts), in an open vessel was stirred with 10 ml conc. hydrochloric acid at room temperature. After 30 min., the product was extracted with toluene, washed with saturated aqueous NaCl and with NaHCO$_3$ solutions and dried. By solvent evaporation a colourless liquid was obtained (17.3 parts, 80%) %Br, 36.9; %P, 6.0; $n_D^{20}$ 1.4925; of low solubility in water and easily soluble in organic solvents. Its I.R., N.M.R. and M.S. identify it as 0,0-diethylphosphonoacetal of dibromoneopentyl glycol. Growth enhancement on white cultures was 8% and on the green ones 41%.

EXAMPLE 8

Bis-0,0-diethylphosphonoacetal of pentaerythritol (7.8 parts) was saponified in aqueous sodium hydroxide (1.4 parts in 300 parts H$_2$O) or barium hydroxide (5.5 parts in 300 parts H$_2$O) at room temperature for 24 hours. The reaction mixture was then passed through the H$^+$-form of a cation exchange resin column, and concentrated under vacuum, thus obtaining a colourless viscous syrup (6.6 parts, 96%), %P, 13.8, $n_D^{25}$ 1.4687, TGA>200°, identified as bis(0-ethyl-0-hydrogen-phosphonoacetal) of pentaerythritol. The compound is non-toxic to white and green calli and has a growth stimulation effect of 49% on the green callus, and 26% on the white ones.

EXAMPLE 9

69.7 parts of 0,0-[1-diethylphosphonomethyl]-pentaerythritol (monophosphonoacetal of pentaerythritol) in 10 parts of anhydrous pyridine were treated with 0.6 parts of benzoyl chloride and left for 24 hours at room temperature. The reaction mixture was slowly mixed with 100 parts of water and left for one hour at 4° C. The product crystallizes as white needles, m.p. 91°–2°; Found: P, 5.8; Calc.: P, 6.1%. Chemically and spectroscopically defined as the appropriate debenzoate derivative of the substrate.

EXAMPLE 10

A reaction similar to reaction 9 but using methyl isocyanate as the reagent, was carried out for 24 hours. There was obtained a yellowish oil, $n_D^{30}$ 1,4717, identified as the urethane of methyl carbamoyl derivative by N.M.R., I.R. and M.S.

We claim:

1. A phosphonoacetal of the formula

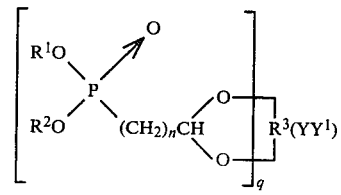

wherein
$R^1$ is an alkyl group having from 1–3 carbon atoms;
$R^2$ is selected from the group consisting of hydrogen and the cations NH$_4^+$, Na$^+$, K$^+$, Ca$^{2+}$, Cu$^{2+}$, and $R^1$;
n is an integer from 0 to 2;
q is an integer from 1 to 3;
$R^3$ is a residue of a polyhydric alcohol having from 2–6 carbon atoms;
Y and $Y^1$ are each hydrogen hydroxyl, carbinol, methyl halogen, or methyl carbamoyl.

2. A compound according to claim 1 wherein $R^1$ is ethyl or methyl.

3. A compound according to claim 1 wherein n is 1 or 2.

4. A compound according to claim 1 wherein q is 2.

5. A compound according to claim 1 wherein $R^3$ is a residue of ethylene glycol.

6. A compound according to claim 1 wherein $R^3$ is a residue of propane-1,3-diol.

7. A compound according to claim 1 wherein $R^3$ is a residue of pentaerythritol.

8. A compound according to claim 1 wherein $R^3$ is a residue of dibromoneopentyl glycol.

9. A compound according to claim 1 wherein $R^3$ is a residue of galactitol.

10. A compound according to claim 1 wherein $R^3$ is a residue of mannitol.

11. A compound according to claim 7 wherein $R^2$ is a hydrogen atom or Na$^+$.

12. A compound according to claim 7 wherein Y and Y¹ are substituted OH groups.

13. A plant growth regulating composition containing or agricultural carrier and as active ingredient an effective quantity of a compound defined in claim 1.

14. A compound according to claim 1 wherein n is 0 or 2.

15. A compound according to claim 1 wherein $R^3$ is a residue of a polyhydric alcohol having three carbon atoms.

* * * * *